(12) United States Patent
Hallundbæk et al.

(10) Patent No.: US 9,045,974 B2
(45) Date of Patent: Jun. 2, 2015

(54) BUBBLE LOGGING TOOL

(75) Inventors: Jørgen Hallundbæk, Græsted (DK); Ulrik Weiland Robenhagen, Frederiksberg (DK); Jimmy Kjærsgaard-Rasmussen, Birkerød (DK)

(73) Assignee: WELLTEC A/S, Allerod (DK)

( * ) Notice: Subject to any disclaimer, the term of this patent is extended or adjusted under 35 U.S.C. 154(b) by 534 days.

(21) Appl. No.: 13/505,183

(22) PCT Filed: Oct. 29, 2010

(86) PCT No.: PCT/EP2010/066448
§ 371 (c)(1),
(2), (4) Date: Apr. 30, 2012

(87) PCT Pub. No.: WO2011/051432
PCT Pub. Date: May 5, 2011

(65) Prior Publication Data
US 2012/0210779 A1 Aug. 23, 2012

(30) Foreign Application Priority Data

Oct. 30, 2009 (EP) .................................... 09174666
Dec. 23, 2009 (EP) .................................... 09180570

(51) Int. Cl.
*E21B 47/10* (2012.01)
*E21B 47/00* (2012.01)
*G01N 21/954* (2006.01)

(52) U.S. Cl.
CPC ........... *E21B 47/102* (2013.01); *E21B 47/0002* (2013.01); *G01N 21/954* (2013.01)

(58) Field of Classification Search
CPC ........................................................ E21B 47/102
USPC ........................................................ 73/152.18
See application file for complete search history.

(56) References Cited

U.S. PATENT DOCUMENTS

| 4,701,051 | A | * | 10/1987 | Buchhave et al. | ............. 356/336 |
| 4,997,272 | A | * | 3/1991 | Dopheide et al. | ............. 356/28.5 |
| 5,543,972 | A | * | 8/1996 | Kamewada | .................... 359/834 |
| 5,790,185 | A | | 8/1998 | Auzerais et al. | |
| 6,411,377 | B1 | * | 6/2002 | Noguchi et al. | ............. 356/237.4 |
| 7,933,018 | B2 | * | 4/2011 | Vannuffelen et al. | ......... 356/432 |
| 2007/0108378 | A1 | | 5/2007 | Terabayashi et al. | |

FOREIGN PATENT DOCUMENTS

DE 199 45 852 3/2000
WO WO 2007/054800 5/2007

OTHER PUBLICATIONS

International Search Report for PCT/EP2010/066448, mailed Jan. 31, 2011.
International Preliminary Report on Patentability for PCT/EP2010/066448, mailed Oct. 19, 2011.

* cited by examiner

*Primary Examiner* — John Fitzgerald
(74) *Attorney, Agent, or Firm* — Nixon & Vanderhye P.C.

(57) ABSTRACT

The present invention relates to a logging tool for detecting an element present in a fluid surrounding the tool downhole. The element is at least one bubble, particle or debris in the fluid, and the tool has a longitudinal axis and comprising an emitting device for emitting radiation, a lens for transmitting the radiation in a predetermined pattern of radiation, and a receiving device.

16 Claims, 8 Drawing Sheets

BUBBLE LOGGING TOOL

This application is the U.S. national phase of International Application No. PCT/EP2010/066448, filed 29 Oct. 2010, which designated the U.S. and claims priority to EP Application No. 509174666.9, filed 30 Oct. 2009, and EP Application No. 09180570.5, filed 23 Dec. 2009, the entire contents of each of which are hereby incorporated by reference.

FIELD OF THE INVENTION

The present invention relates to a logging tool for detecting an element present in a fluid surrounding the tool downhole. The element is at least one bubble, particle or debris in the fluid, and the tool has a longitudinal axis and comprising an emitting device for emitting radiation, a lens for transmitting the radiation in a predetermined pattern of radiation, and a receiving device.

BACKGROUND ART

In order to optimise production in a well, it is important to know the characteristics of the well fluid, such as the density, the amount of particles and gas/water bubbles, the temperature and the velocity.

Velocity measurements can be performed in different ways. One way is to measure the capacitance between two pairs of electrodes, and by comparing the measurements conducted in the two pairs, the velocity of the fluid can be calculated. However, such measurements are based on a presumption that the fluid is distributed evenly, which is not always the case. Another way to measure velocity is to use tracers in the fluid, which contaminates the fluid.

DESCRIPTION OF THE INVENTION

It is an object of the present invention to provide a downhole tool capable of identifying at least part of the characteristics of the fluid present in a well.

It is moreover an object to provide a tool capable of outlining or picturing the hardware and the casing wall.

The above objects, together with numerous other objects, advantages, and features, which will become evident from the below description, are accomplished by a solution in accordance with the present invention by a logging tool for detecting an element present in a fluid surrounding the tool downhole, the element being at least one bubble, particle or debris in the fluid, the tool having a longitudinal axis and comprising:
  an emitting device for emitting radiation,
  a lens for transmitting the radiation in a predetermined pattern of radiation, and
  a receiving device,
wherein the pattern of radiation is reflected on an object, such as a casing wall, and the reflected radiation is received in the receiving device, and when an element is present in the fluid outside the emitting device, part of the pattern of radiation is scattered and/or reflected by the element, resulting in a change in the pattern of radiation and a first measurement.

The above logging tool makes it possible to count the number of gas or water bubbles in an oil containing fluid in the well, and to measure the size of the bubbles and thus determine certain characteristics of the fluid, such as its velocity.

The first measurement may be conducted at a first time, and a second measurement may be conducted at a second time.

By having a first and a second measurement and a time interval between the two measurements, the measurements can be used to determine the velocity of the fluid by comparing the measurements or images, and it is then possible to first calculate the distance between two elements and then the velocity of the fluid.

In an embodiment, the emitting device may be arranged inside the lens.

Furthermore, the lens may enclose the emitting device.

In addition, the pattern of radiation may be irradiated substantially transverse to the longitudinal axis of the tool.

Moreover, the logging tool may be a bubble count tool.

The logging tool may comprise a bubble generator creating bubbles in the fluid. If the velocity of the fluid is to be determined, and there are no bubbles in the fluid, the bubble generator creates bubbles.

The logging tool may furthermore comprise a bubble generator which is a second emitting device arranged in the tool upstream of the first emitting device.

The second emitting device may emit radiation high enough to evaporate oil fractions in the fluid and thereby create gas bubbles.

In one embodiment, the logging tool may comprise a bubble generator comprising a chamber of pressurised gas which, when released trough a valve in the generator, creates gas bubbles in the fluid.

A first measurement may be conducted in a first position at a first time, and a second measurement is conducted in the first position of the tool by receiving the reflected radiation at a second point in time.

The emitting device may emit radiation at a power of at least 5 W or at least 5 kW, and the emitting device may be a laser.

In another embodiment, the logging tool may further comprise a driving unit for moving the tool forward in the well.

Moreover, the pattern may be a line.

Furthermore, the driving unit may be a conveying unit arranged inside the tool.

Additionally, the receiving device may be a recording device.

The emitting device may emit radiation in a direction transverse to a longitudinal axis of the tool.

The tool may furthermore comprise a mirror device arranged so that it directs the radiation towards the receiving device.

In yet one embodiment, the logging tool may further comprise a mirror device for reflecting the pattern reflected by the object before the pattern is received in the receiving device.

This mirror may be conical.

A measurement may be conducted at a rate of 10 to 200 measurements per second, preferably at a rate of 20 to 100 measurements per second, and more preferably at a rate of 20 to 50 measurements per second.

This invention also relates to a method comprising the steps of inserting a logging tool according to any of the preceding claims into a well, the well comprising a fluid; emitting a pattern of radiation in a direction of an object; part of the radiation being scattered and/or reflected by an element being a bubble of gas or water, a particle or a debris in the fluid between the tool and the object; another part of the radiation being reflected by the object; detecting the reflected pattern; and analysing the reflected pattern in order to identify the element.

The method may further comprise the step of counting the elements.

Moreover, the method may further comprise the steps of identifying the element in a second measurement, and measuring a distance by which the element moves from the first measurement to the second measurement, Finally, the method may further comprise the step of calculating a velocity of the element and thus the velocity of the fluid.

BRIEF DESCRIPTION OF THE DRAWINGS

The invention and its many advantages will be described in more detail below with reference to the accompanying schematic drawings, which for the purpose of illustration show some non-limiting embodiments and in which.

All the figures are highly schematic and not necessarily to scale, and they show only those parts which are necessary in order to elucidate the invention, other parts being omitted or merely suggested.

DETAILED DESCRIPTION OF THE INVENTION

Figure 1A:
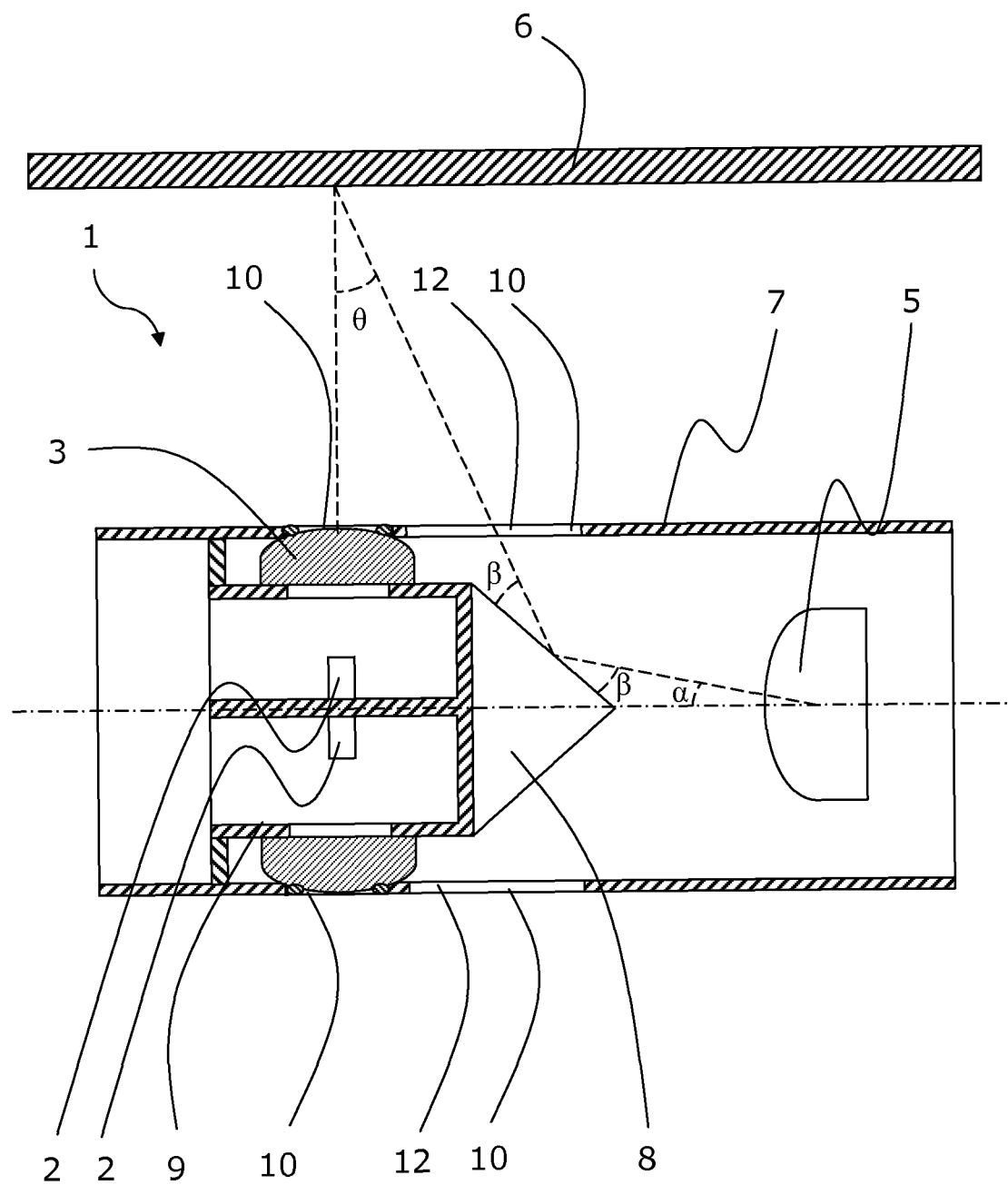
FIG. 1A shows a partly cross-sectional view of a logging tool according to the invention viewed from a side.
Figures 4A, 4B:
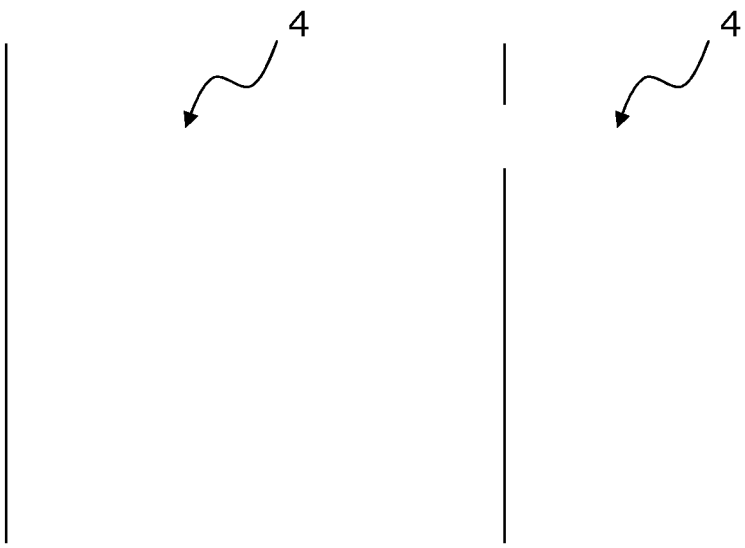
FIG. 4A shows a pattern in the form of a line.
FIG. 4B shows the line of FIG. 4A in which an element has scattered some of the radiation.
Figure 5A:
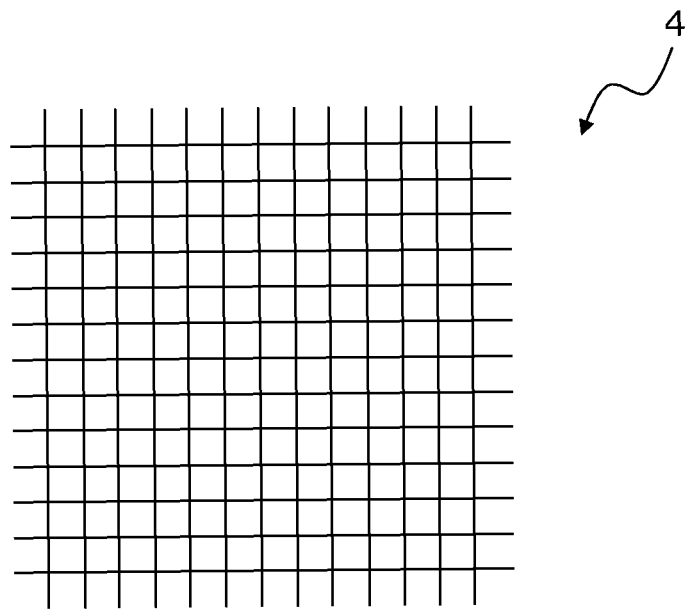
FIG. 5A shows the pattern as a grid.
Figure 5B:
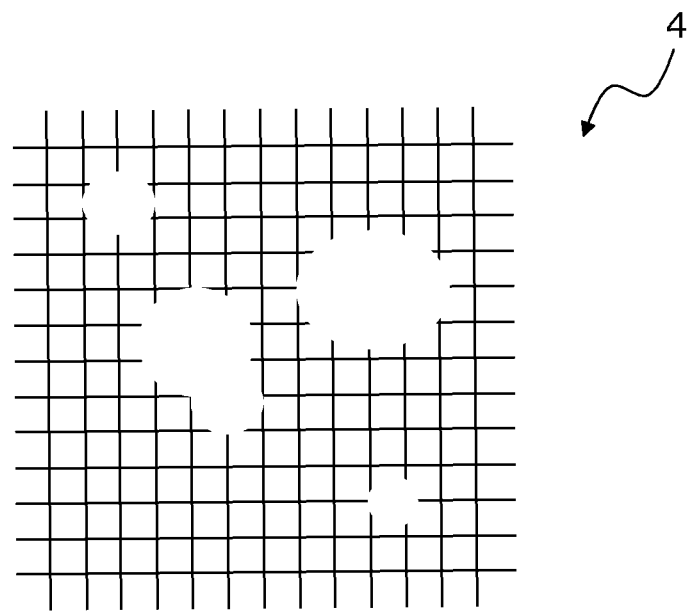
FIG. 5B shows the grid of FIG. 5A in which elements have scattered some of the radiation.
Figure 6:
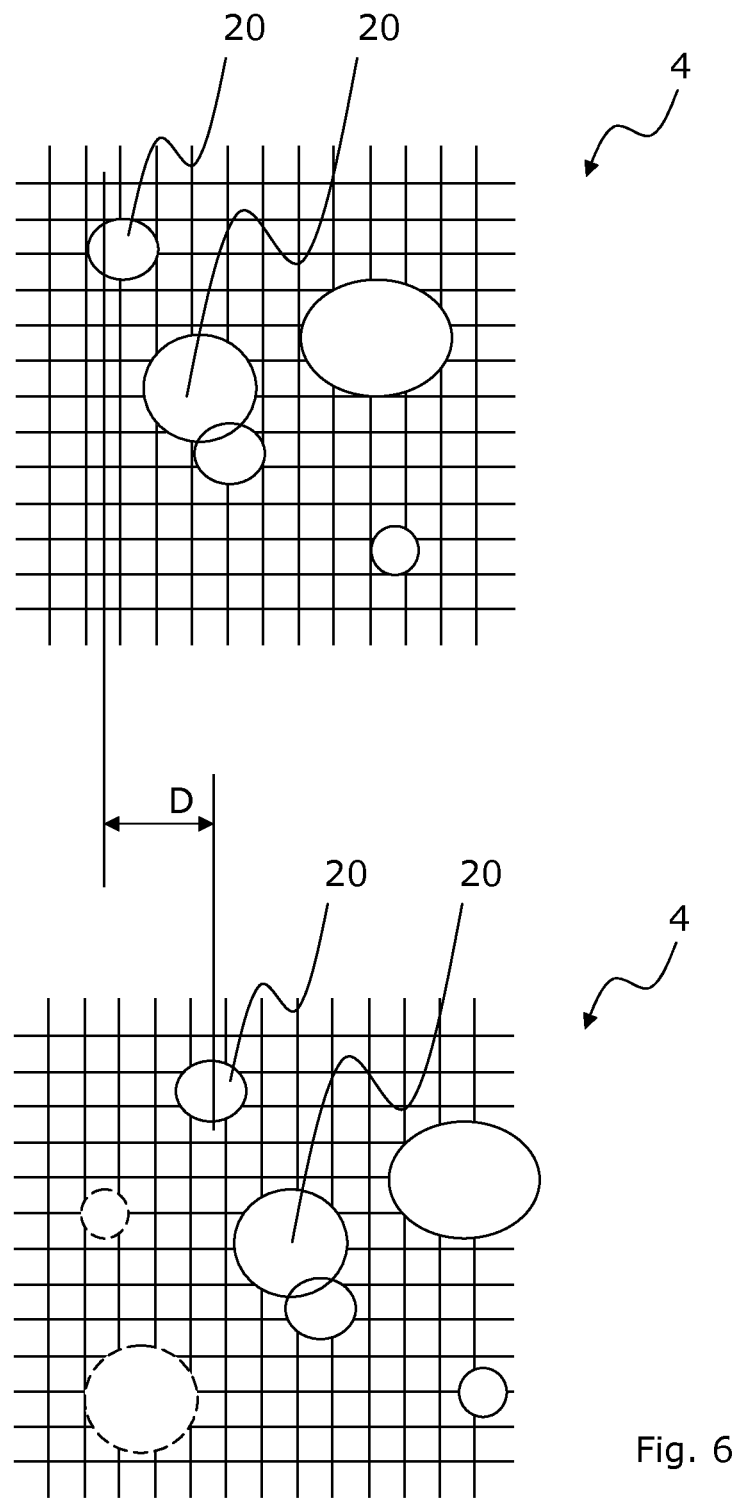
FIG. 6 shows a first measurement and a second measurement which are analysed.

In FIG. 1A, part of a logging tool 1 according to invention is shown. The logging tool 1 is capable of determining an element downhole. The logging tool 1 comprises an emitting device 2 for emitting radiation into a lens 3. The lens 3 transmits the radiation in a predetermined pattern 4 of radiation, such as a line as shown in FIGS. 1A, 1B, 4A and 4B, a grid as shown in FIGS. 5A, 5B and 6, or another suitable pattern. The pattern 4 is reflected on the object 6, which is the inside wall of the casing or borehole, and is subsequently detected by a receiving device 5.

In the following, the invention is explained on the basis of an object 6 present in the well, such as a valve arranged as part of the casing wall, a sleeve, a packer or the like hardware elements in a well. Furthermore, the invention is explained on the basis of an element present in the well fluid, such as a gas or water bubble, a debris, a particle, such as a swarf or a fragment of the formation, or the like element present in the well fluid.

Figure 3:
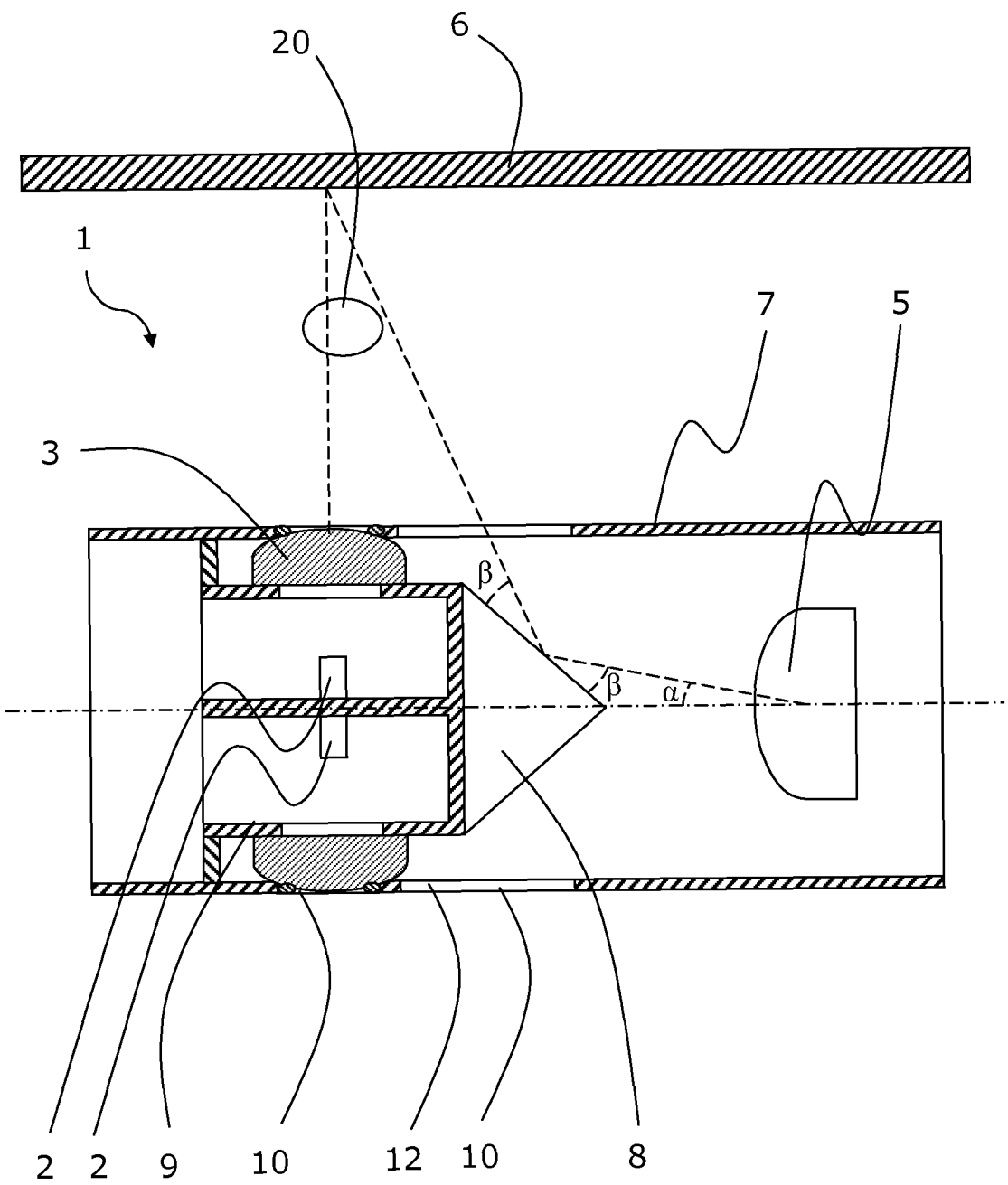
FIG. 3 shows an element in the cross-sectional view of FIG. 1A.

As mentioned, the pattern 4 of radiation is reflected on an object 6, and the reflected radiation is received in the receiving device 5. If an element 20 is present outside the emitting device 2, as shown in FIG. 3, part of the radiation is scattered and/or reflected, meaning that the receiving device 5 is no longer able to detect the line in that part, as illustrated in FIG. 4B. The line may, however, still appear in the image/measurement as a weaker line. In FIG. 3, the element blocks the way of a part of the radiation before the radiation is reflected on the object 6. The same would happen if the element blocked the way of the reflected radiation.

The FIGS. 4A-6 are illustrations of the radiation pattern 4, and the black lines illustrate the lines of radiation which, in an image received by the receiving device 5, will appear as bright lines while the white background will appear as a black background since the only light downhole is the light coming from the emitting device 2. This means that the parts of the lines missing due to the scattering by the element will appear as black shadows in almost the same colour as the black background.

The receiving device 5 is a camera, an image sensor or the like processor. The receiving device 5 may have a lens 3 provided in front of the camera viewed in relation to the emitting device 2.

Figure 4C:
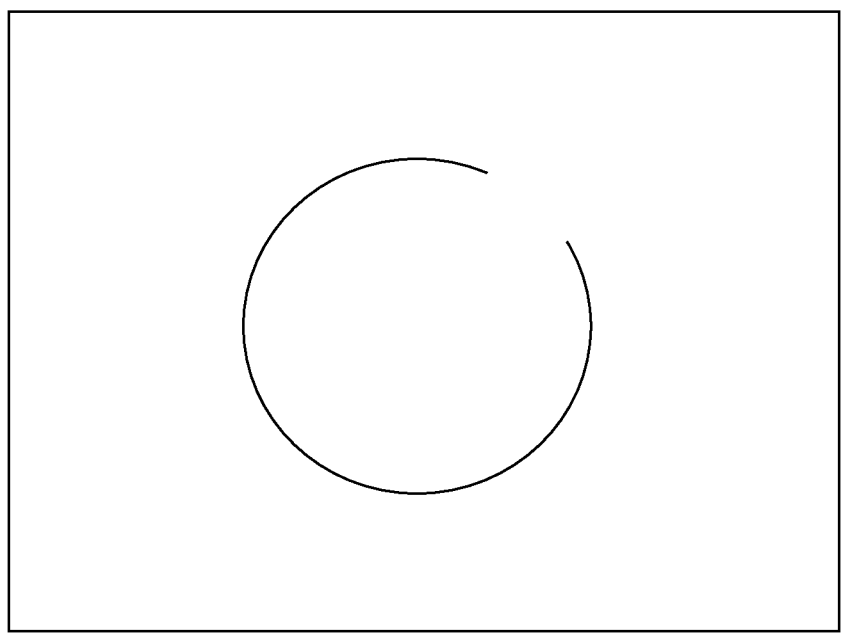
FIG. 4C shows the line of FIG. 4B as it is received in the receiving device.

The logging tool 1 comprises an elongated housing 7 with a plurality of slots or openings 10 allowing radiation in the form of light to be emitted from the tool and enter the tool again. Inside the housing 7, the torus-shaped lens 3 is illuminated from within by the emitting device 2. In order to illuminate the whole lens 3, several emitting devices 2 are arranged inside the torus. In FIG. 1A, twenty emitting devices 2 are arranged inside the lens 3. The lens 3 guides the radiation into a pattern 4, such as a line, and irradiates the object 6 in that pattern. The pattern 4 is reflected by the surface of the object 6 and is returned in an angle 8 so as to be reflected by a mirror 8 before being received in the receiving device 5. The mirror 8 is cone-shaped, and in this embodiment, the pattern 4 is a line which is reflected as a circle by the mirror, as illustrated in FIG. 4C. The mirror 8 is mounted onto the housing 7 by means of a mounting device 9 onto which the emitting device 2 is also fastened. The mounting device 9 is provided with a circumferential slot allowing the radiation of the emitting devices 2 to illuminate the lens 3. Having a mirror 8 makes it possible to arrange the receiving device 5 axially displaced in relation to the lens 3.

Thus, the lens 3 has a radial extension transverse to the longitudinal extension of the tool 1. The emitting devices 2 are arranged so that they irradiate the lens 3 in a radial direction. The mirror 8 is arranged on one side of the lens 3 at an axial distance from the lens 3 in relation to the axis of the tool 1 and tapers away from the emitting devices 2 and the lens. The receiving device 5 is arranged at an axial distance from the mirror 8 even further away from the lens 3.

In another embodiment, only three emitting devices 2 are arranged inside the lens 3. Such emitting devices 2 must have a wider emitting range in order to illuminate the whole lens 3.

A sealing means 11 in the form of an O-ring is arranged between the lens 3 and the housing 7 in order to seal off the inside of the tool 1. Furthermore, the slot 10 through which the reflected radiation enters the housing again may be provided with a window 12 also sealing off the inside of the housing, but also letting the light through.

In another embodiment, the surrounding part of the tool 1 is a glass housing surrounding a frame part of the tool, which in this case is also the mounting device 9 of the tool.

Figure 1B:
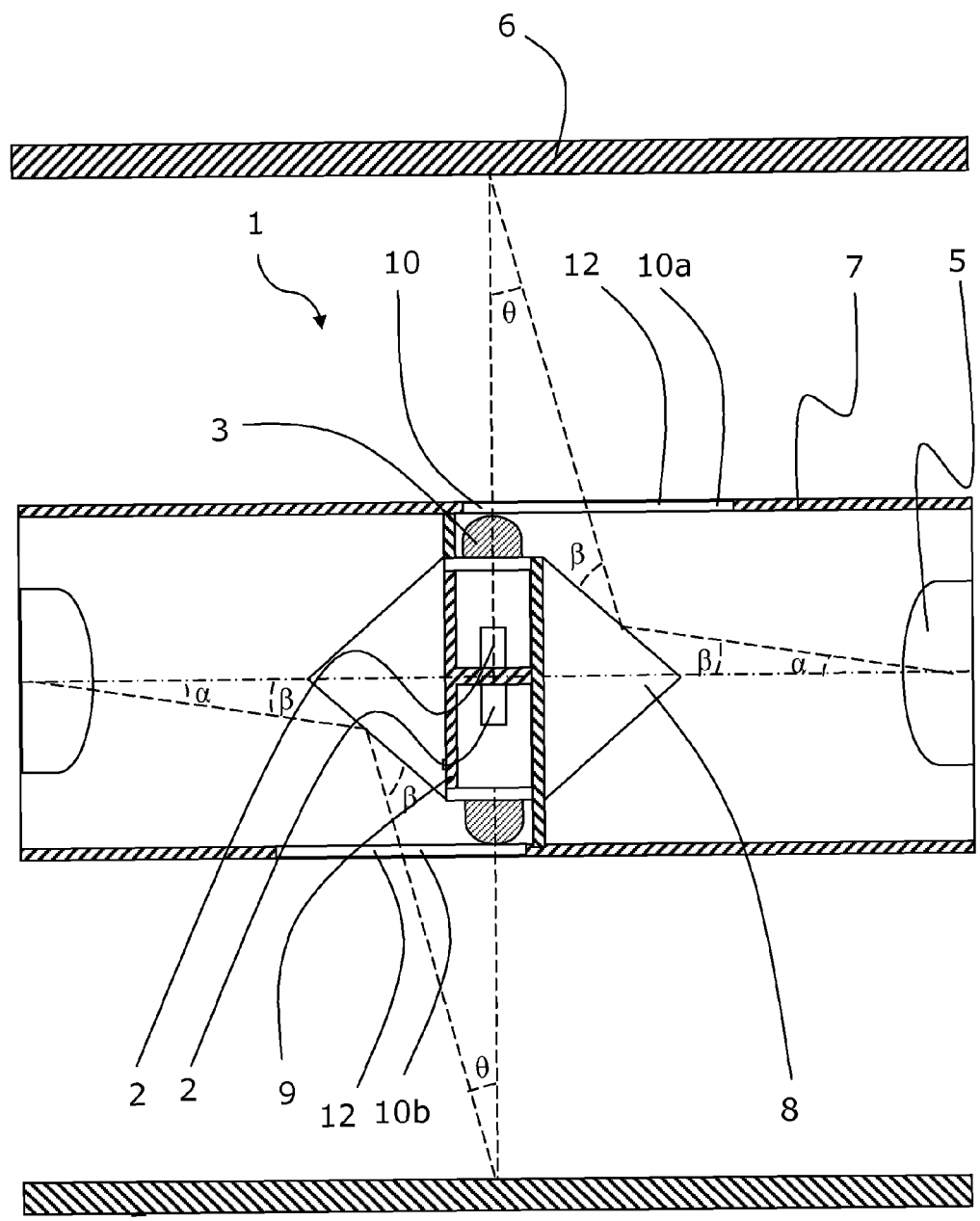
FIG. 1B shows a partly cross-sectional view of another embodiment of the logging tool according to the invention viewed from a side.

In FIGS. 1A and 1B, the lens 3 generates a radiation pattern 4 in the form of a line and is a plano-convex cylinder lens. However, the lens 3 may be any suitable lens capable of generating a pattern 4, such as a line, a grid, etc.

Another embodiment of the tool 1 is shown in FIG. 1B, in which embodiment the tool has two mirrors 8 and two receiving devices 5 positioned opposite each other so that a mirror and a receiving device are positioned on each side of the lens 3. In this embodiment, the mounting device 9 has a frame configuration providing a strong tool design. The frame has openings 10 displaced in relation to one another so that a first opening 10a is displaced in relation to a second opening 10b. Each opening 10 is adapted to both emit radiation and let in reflected radiation to be reflected by the mirror 8 and transmitted into the receiving device 5. Each of the receiving devices 5 receives only part of the reflected radiation so that one part of the pattern 4 is received in one receiving device 5 and another part is received in the other receiving device 5. When these parts of the reflected pattern are joined, the whole pattern can subsequently be processed, as explained below.

The entire mounting device 9 may be surrounded by only one glass housing providing a simple encapsulation of the mounting device and a design which seals off the tool 1 towards the outside well fluid in a simple manner.

The receiving device 5 of FIGS. 1A and 1B receives the reflected line as a circle or parts of a circle due to the conical shape of the mirror 8. The receiving device 5 receives light from a small part of the casing, and each point on the object 6, e.g. the inside of the casing, is mapped to a point between two concentric circles in the two-dimensional image plane. Thus, the radiated line in the image corresponds to a plurality of points on the casing.

In this embodiment, the pattern 4 is a line emitted as a circle all the way around the tool 1 towards the inside of the casing to scan the casing. The pattern 4 may be any kind of pattern emitted as a closed contour on an object 6, in the illustrated example as a circle which is received in the tool 1 again as a circle if the inside of the casing wall is smooth.

Moreover, an image sensor connected with the receiving device 5 converts the image of a circle into data. In FIG. 4C, the circle is broken since a piece of the circle is not detected by the receiving device 5. The reason for this is that the emitted line has been reflected and scattered in/on the element. If the element is a gas or water bubble, the radiation is scattered in multiple directions by the bubble, leaving the radiation reflected in the direction of the receiving device 5 with too little energy to be detected by the receiving device. Furthermore, if the element is a debris or a particle, the radiation is reflected on the surface and is scattered in multiple directions due to its uneven surface.

In this way, it is possible to determine the number of elements by counting the parts of the line of radiation which are missing due to the scattering of the element.

If there are too many elements present in the fluid, the elements overlap, and the break in the line of radiation only appears one time for several elements, resulting in an imprecise count of the elements. Also, when having elements with an extension which is smaller than the distance between the line of radiation and the reflected line, one element is counted twice, as shown in FIG. 3. In this event, the pattern 4 of radiation could be changed into a grid, as shown in FIG. 5A, and in this way, several elements are shown as disrupting the grid lines several times, as can be seen in FIG. 5B. In FIG. 5B, two elements overlap, which is very difficult to see. However, by recognising the circumferences of the elements, as shown in the top illustration of FIG. 6, it is possible to determine the number of elements. In this way, it will never occur that several elements are mistakenly counted as only one element, and no elements will be counted twice.

When the measurements or images are combined in pairs of two in a sequence of images received by the receiving device 5 at a predetermined sample rate, as shown in FIG. 6, it is possible to determine the distance between the elements, and when comparing this distance with the known sample rate, it also becomes possible to determine the velocity of the elements. By knowing the velocity of the element flowing in the fluid, it is also possible to make a very good estimation of the fluid velocity.

As can be seen in FIG. 6, five elements are shown in both the top and the bottom image, creating a recognisable pattern 4. The "new" elements, which are not yet visible in the top image, are illustrated by dashed lines. In order to use image/pattern recognition, it is necessary to determine the circumference of each element. When it has been determined which position and size of a circumference provide the best fit for each element, the image recognition can begin. When a pattern 4 of elements is recognised in an image and in the subsequent image, it is possible to estimate the distance between each element from the first measurement to the second measurement. The velocity of small and large elements will not be exactly the same. However, by calculating the mean velocity, it is possible to make a good estimation of the velocity of the fluid.

In this way, the logging tool 1 scans the elements in the fluid in order to determine the characteristics of the fluid. The 1 tool is mainly maintained in the same position when conducting a sequence of measurements and the element to be scanned passes the tool. When conducting a sequence of measurements, each element may be irradiated several times at different positions on the element.

Figure 2:
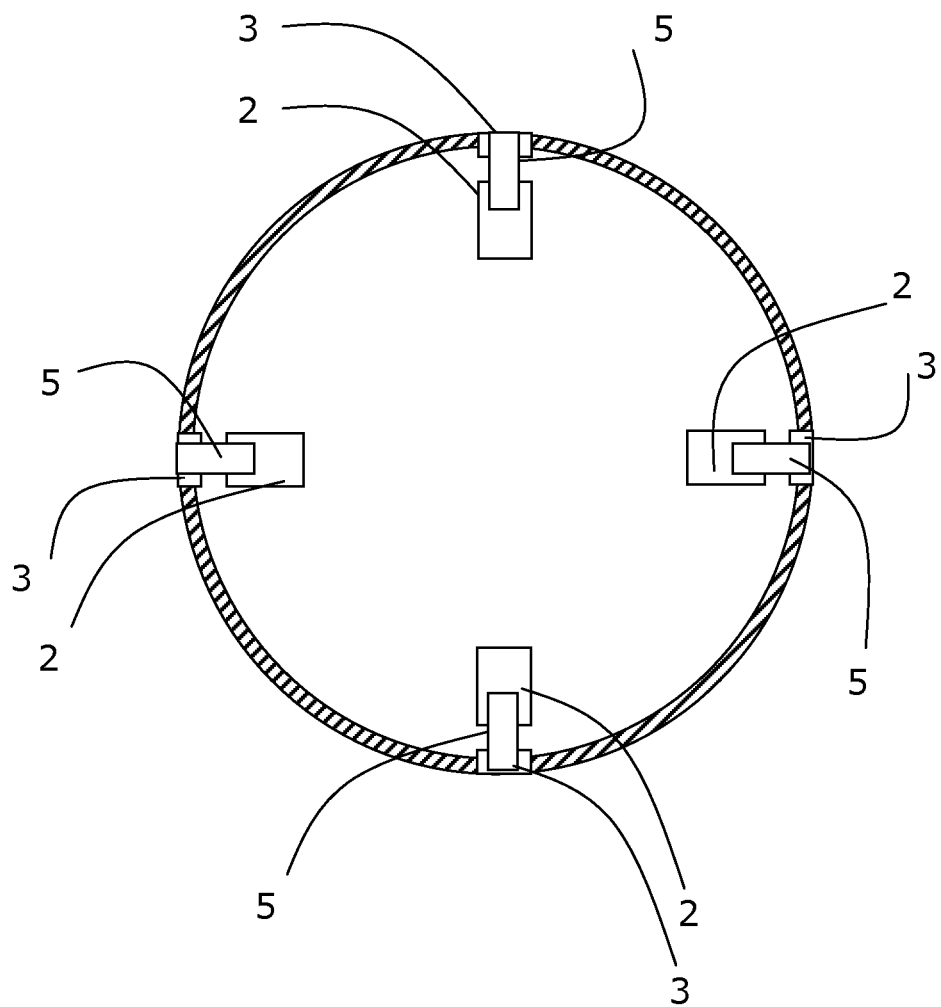
FIG. 2 shows a partly cross-sectional view of another embodiment of the logging tool viewed from one end.

In FIG. 2, the logging tool 1 comprises four lenses 3 arranged spaced apart along the periphery of the tool housing 7. Each lens 3 is illuminated by an emitting device 2 situated radially behind the lens in a direction towards the centre of the tool 1. Each lens 3 is capable of transmitting a line radially, the lines of the four lenses thus overlapping each other and together defining one circumferential line. Next to each lens 3 in the axial extension of the tool, a receiving device 5 is arranged for receiving the line when reflected by the object 6. In the embodiment of FIG. 2, no mirror is needed to scan the object 6 since each receiving device 5 is arranged next to a lens 3 receiving the reflected radiation radially.

In some cases, more lenses 3, emitting devices 2 and receiving devices 5 may be needed, depending on the object 6 and the elements, the distance to the object, and the condition of the fluid in the well. The more transparent the well fluid, the less illumination is needed for detecting the elements properly.

The lens 3 and the emitting device 2 may be arranged in the tool 1 as one unit, e.g. comprised in a line generator. Furthermore, the tool 1 may comprise several lenses 3 for each emitting device 2, resulting in the creation of a grid, as shown in FIG. 5A, or the lens may be covered in order to create the grid pattern 4. In another embodiment, the emitting device 2 comprises a grid generator.

Figure 7:
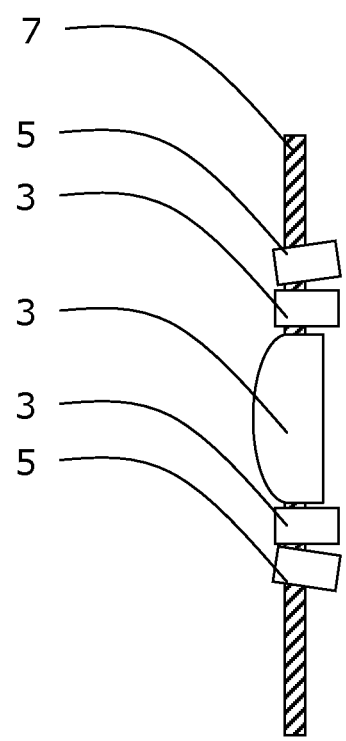
FIG. 7 shows a partly cross-sectional view of yet another embodiment of the tool.

As shown in FIG. 7, the tool 1 may comprise several receiving devices 5 to obtain several measurements concerning the same elements at the same time. As can be seen, the cameras are angled towards the lens 3 and are thus able to detect the same pattern 4 from different angles, creating a three-dimensional image of the element(s). In another embodiment, the pattern 4 may be created by a grid generator arranged behind the lens 3, as shown in FIG. 7.

The pattern of radiation may also be emitted in front of the tool 1 at an angle and thus still be reflected on the casing wall. However, it is easier to analyse the measurements and count the elements and/or calculate the distance between the elements if the radiation is emitted from the side of the tool 1 in an angle substantially perpendicular to the longitudinal direction of the tool.

The images may be received and at least partly processed by the receiving device 5 at a rate of 10-200 images per second, preferably 20-100 images per second, and even more preferably 20-50 images per second. When an image is received, it is converted into data, such as electronic signals. This data is compared to the data of the image previously taken, and only the differences between the data are communicated to the top of the well or above surface to reduce the total amount of data.

The data may also be compressed in conventional ways before being sent to the top of the well or to the surface. It may also be downloaded into a buffer, such as a data memory. If no change is detected, the logging tool 1 may transmit a signal to the top of the well that there is no change.

The mirror 8 may have any suitable shape, such as a pyramid shape, a semi-sphere or the like.

The emitting device 2 emits electromagnetic radiation with a frequency of $10^{11}$-$10^{19}$ Hz, such as X-rays, UV, visible light and infrared light. The emitting device 2 may thus be a laser or another radiation device.

The emitting device 2 emits radiation at a radiation energy of between 5 W and 10 kW, depending on the visibility in the well fluid and on how much energy is absorbed in the emitting device, such as a line generator or a grid generator, in order to emit the radiation only in the predetermined pattern 4. When creating a grid, up to 90% of the radiation may be absorbed. When the emitting device 2 is used as a bubble generator, the energy level is between 50 W and 1000 W since almost all the energy is transmitted into the fluid to evaporate some of the fluid, creating bubbles.

When the well fluid to be penetrated by the radiation of the logging tool 1 is water or gas, light with a frequency of 4E14 Hz or wavelength of 750 nm is sufficient. However, when the fluid is primarily oil, the emitted radiation could be another type of radiation, such as radiation closer to the infrared area or closer to UV.

The receiving device 5 may be a camera or an image sensor converting an optical image/pattern into an electric signal.

The tool 1 may also comprise a driving unit for moving the tool.

By fluid or well fluid is meant any kind of fluid which may be present in oil or gas wells downhole, such as natural gas, oil, oil mud, crude oil, water, etc. By gas is meant any kind of gas composition present in a well, completion or open hole, and by oil is meant any kind of oil composition, such as crude oil, an oil-containing fluid, etc. Gas, oil, and water fluids may thus all comprise other elements or substances than gas, oil, and/or water, respectively.

By a casing is meant any kind of pipe, tubing, tubular, liner, string, etc. used downhole in relation to oil or natural gas production.

In the event that the tools are not submergible all the way into the casing, a downhole tractor can be used to push the tools all the way into position in the well. A downhole tractor is any kind of driving tool capable of pushing or pulling tools in a well downhole, such as a Well Tractor®.

Although the invention has been described in the above in connection with preferred embodiments of the invention, it will be evident for a person skilled in the art that several modifications are conceivable without departing from the invention as defined by the following claims.

The invention claimed is:

1. A logging tool for detecting an element present in a fluid surrounding the tool downhole, the element being at least one gas/water bubble, particle or debris in the fluid, the tool having a longitudinal axis and comprising:
    an emitting device to emit radiation,
    a lens to transmit the radiation in a predetermined pattern of radiation, and
    a receiving device,
wherein the pattern of radiation is reflected on an object and the reflected radiation is received in the receiving device, and when the element is present in the fluid outside the emitting device, part of the pattern of radiation is scattered and/or reflected by the element, resulting in a change in the pattern of radiation and a first measurement.

2. A method according to claim 1, wherein the object is a casing wall.

3. A logging tool according to claim 1, wherein the first measurement is conducted at a first time and a second measurement is conducted at a second time.

4. A logging tool according to claim 1, wherein the emitting device emits radiation at a power of at least 5 W.

5. A logging tool according to claim 1, wherein the emitting device is a laser.

6. A logging tool according to claim 1, wherein the emitting device emits radiation in a direction transverse to a longitudinal axis of the tool.

7. A logging tool according to claim 1, further comprising a mirror device for reflecting the pattern reflected by the object before the pattern is received in the receiving device.

8. A logging tool according to claim 1, wherein a measurement is conducted at a rate of 10 to 200 measurements per second, preferably at a rate of 20 to 100 measurements per second, and more preferably at a rate of 20 to 50 measurements per second.

9. A logging tool according to claim 1, further comprising a bubble generator creating bubbles in the fluid.

10. A logging tool according to claim 9, further comprising a bubble generator comprising a chamber of pressurised gas which, when released trough a valve in the generator, creates gas bubbles in the fluid.

11. A logging tool according to claim 9, further comprising a bubble generator being a second emitting device arranged in the tool upstream of the first emitting device.

12. A logging tool according to claim 11, wherein the second emitting device emits radiation high enough to evaporate oil fractions in the fluid and thereby create gas bubbles.

13. A method comprising:
    inserting a logging tool according to claim 1 into a well, the well comprising a fluid,
    emitting a pattern of radiation in a direction of an object,
    part of the radiation being scattered and/or reflected by at least one element being a bubble of gas or water, a particle or a debris in the fluid between the tool and the object,
    another part of the radiation being reflected by the object,
    detecting the reflected pattern, and
    analysing the reflected pattern in order to identify the at least one element.

14. A method according to claim 13, further comprising counting said at least one element.

15. A method according to claim 13, further comprising:
    identifying the at least one element in a second measurement, and
    measuring a distance by which the at least one element moves from the first measurement to the second measurement.

16. A method according to claim 13, further comprising calculating a velocity of the at least one element and thus the velocity of the fluid.

* * * * *